United States Patent [19]
Osborn

[11] 4,197,857
[45] Apr. 15, 1980

[54] SYSTEM FOR MEASUREMENT OF OXYGEN UPTAKE AND RESPIRATORY QUOTIENT

[75] Inventor: John J. Osborn, Tiburon, Calif.

[73] Assignee: Research Development Corporation, San Francisco, Calif.

[21] Appl. No.: 894,189

[22] Filed: Apr. 6, 1978

[51] Int. Cl.² ............................................. A61B 5/08
[52] U.S. Cl. .................................. 128/718; 128/730; 73/421.5 R; 422/84
[58] Field of Search ...................... 128/2.07, 2.08, 2 C, 128/718, 719, 750; 73/421.5 R; 23/232 R, 232 B; 422/83, 84

[56] References Cited
U.S. PATENT DOCUMENTS

| 3,661,528 | 5/1972 | Falk | 128/2.07 X |
| 3,965,749 | 6/1976 | Hadden et al. | 73/421.5 R |

FOREIGN PATENT DOCUMENTS 1959244 2/1973 Fed. Rep. of Germany .......... 128/2.08

*Primary Examiner*—Lee S. Cohen

*Attorney, Agent, or Firm*—Flehr, Hohbach, Test, Albritton & Herbert

[57] ABSTRACT

A system for measuring the oxygen uptake and respiratory quotient of a patient which employs a high resistance gas flow path in parallel with a pneumotachograph. The high resistance path is connected to each side of the pneumotachograph and a small chamber is included in the high resistance path at each end thereof adjacent its connection to the pneumotachograph. The volume of the high resistance path, together with its resistance relative to that of the pneumotachograph is chosen such that, during respiration of the patient employing the device, the high resistance path will never be completely flushed through in one direction before flow starts in the opposite direction. The high reistance path is chosen to be a constant resistance such that the amount of flow therethrough is proportional to the flow through the pneumotachograph. Thus by sampling and analyzing a small portion of the gas of the two chambers and measuring the amount of gas flow by the pneumotachograph, the exact amount of oxygen uptake can be calculated.

11 Claims, 3 Drawing Figures 4,197,857

SYSTEM FOR MEASUREMENT OF OXYGEN UPTAKE AND RESPIRATORY QUOTIENT

BACKGROUND OF THE INVENTION

The direct measurement of oxygen uptake and respiratory quotient is often of importance in medical research or medical care. Many methods are available to make this measurement, but most of them suffer from serious defects. To make the measurement directly from the airway, it is necessary to know the respiratory minute volume, and also the exact concentration of mean inspired gas and mean expired gas for oxygen and carbon dioxide. The measurement of this mean volume and of the two gas concentrations usually requires bulky spirometers and other large apparatus, or else depends upon high flow past the nose and mouth, with downstream sampling. Alternately, the gas concentrations can be measured continuously during inspiration and expiration with the measured concentrations multiplied by the amount of flow and then integrated to obtain the necessary values; but this requires a gas analyzer of extremely rapid response and very careful control of all flows in the system. Because of the careful control required such systems have not proved very accurate.

SUMMARY OF THE INVENTION AND OBJECTS

The invention is incorporated in a pneumotachograph to which has been added a sampling tube on each side of its resistance means. Each tube is connected to a small chamber and the chambers are interconnected by means of a relatively high constant resistance path having a sufficient volume to prevent complete flushing thereof in one direction before flow starts in another direction by reason of the patient's breathing.

It is, therefore, a general object of the present invention to provide an improved apparatus for measuring oxygen uptake and respiratory quotient.

It is a further object of the present invention to provide such improved apparatus for measuring oxygen uptake and respiratory quotient which permits very accurate such measurements with relatively inexpensive gas analyzers and at the same time without the need of bulky or large apparatus to encumber the patient.

BRIEF DESCRIPTION OF THE DRAWING

FIG. 3 is a sectional view taken along the line 3—3 of FIG. 2, but with the flap closed, showing the construction of the orifice membrane of the additional pneumotachograph.

DETAILED DESCRIPTION OF THE PREFERRED EMBODIMENTS

Figure 1:
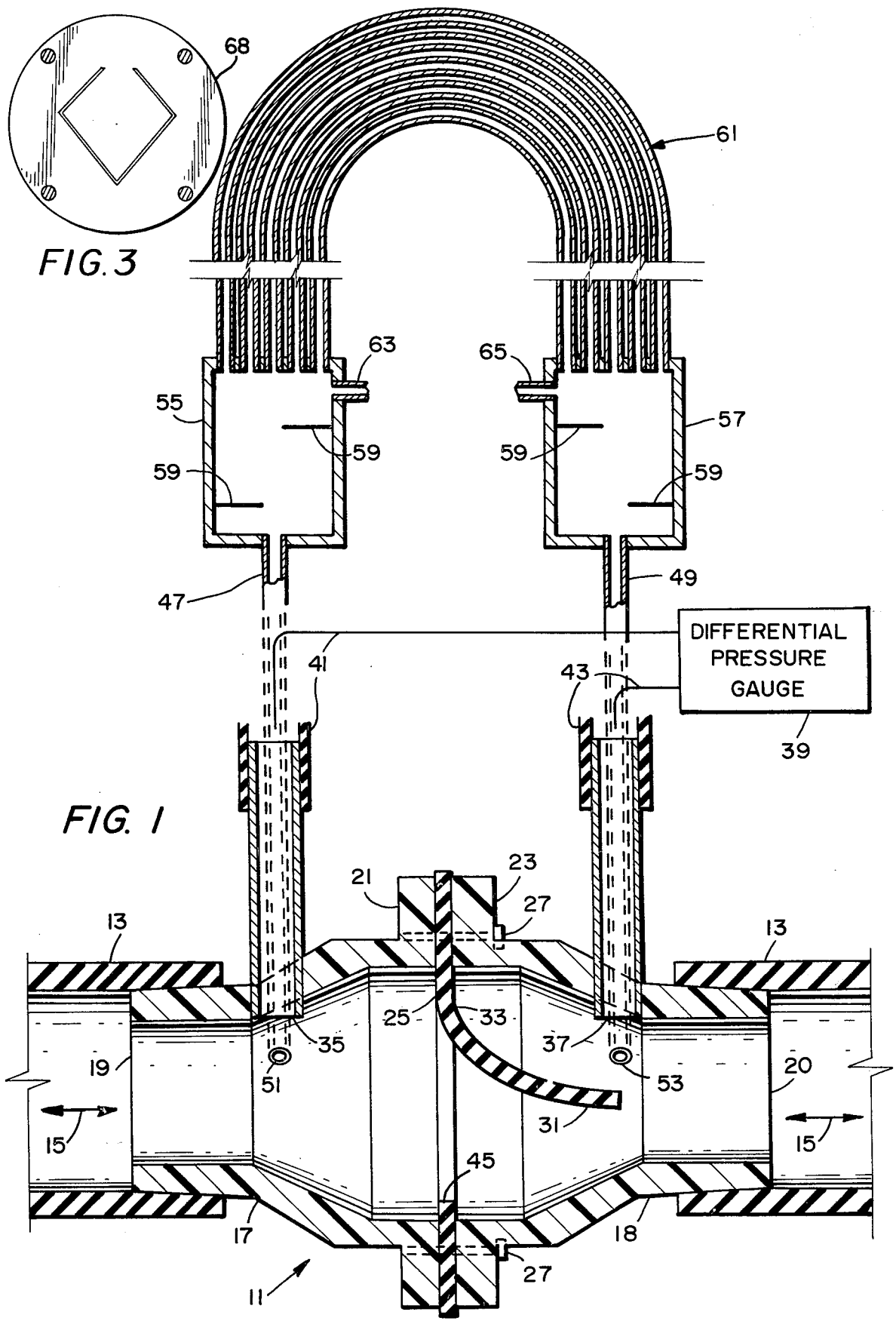
FIG. 1 is a schematic diagram of apparatus for measuring oxygen uptake and respiratory quotient in accordance with the invention wherein the high resistance path incorporates a series of small diameter tubes arranged in parallel.

Referring to FIG. 1 there is shown a pneumotachograph or sensing head 11. Generally, a pneumotachograph is an instrument for measuring flow by measuring the differential pressure across a resistance in the line of flow. The resistance is constant over a wide range of flow so that the pressure can be read directly as a simple function of the differential pressure. The constant resistance may be created by multiple parallel tubes sufficiently small to maintain the flow laminar. Alternatively, the resistance may be created by a moving orifice or other device, keeping in mind that the resistance is to be constant over the range of flow.

The pneumotachograph 11 shown in FIG. 1 is substantially as shown in applicant's co-pending application Ser. No. 779,557, filed Mar. 21, 1977, entitled "Variable Orifice Gas Flow Sensing Head" now U.S. Pat. No. 4,083,245 which application and patent is incorporated herein by reference. As set forth in that application, the sensing head 11 is disposed in a gas flow line 13 through which gas may flow horizontally in the direction of the arrows 15. The head may include inlet and outlet portions 17 and 18 having ports 19 and 20 each of which carries a flange 21, 23 for securing them together. An orifice membrane 25 is retained between the flanges 21,23 by means of screws 27 and the like. Flap 31 is joined integrally with the membrane 25 and hinged at 33.

Pressure ports 35 and 37 are provided in the sensing head 11 and are connected to a differential presure gauge 39 by means of the tubes 41 and 43 so as to permit reading of the gas flow. The apex 45 of the orifice in membrane 25 is disposed at the bottom thereof for easy passage of fluids which may be carried in the line.

While the pneumotachograph 11 set forth above is as described in said U.S. Pat. No. 4,083,245 and is the preferred type of pneumotachograph to be utilized in this invention, it is not entirely necessary that this particular type pneumotachograph be employed. Other constant resistance devices may be substituted.

In addition to the elements set forth above, there are two additional tubes 47 and 49 connected to the pneumotachograph 11 on opposite sides of the membrane 25 at openings 51 and 53 which are disposed in the upper region of the pneumotachograph so as to avoid interference with free fluids which may be carried through the pneumotachograph.

Each of the tubes 47 and 49 connect with a small chamber 55,57 each of which carries a series of baffles 59. The chamber 57 will be employed to sample inspiration gases and the chamber 55 to sample expiration gases.

The opposite ends of the chambers 55 and 57 are connected to the opposite ends of a series of small parallel tubes 61. Tubes 61 are chosen in size to collectively have a rather high resistance compared to that of the pneumotachograph 11 and to individually be of sufficiently small internal diameter (e.g. 3 mm.) that the flow through it is laminar. In some instances it is satisfactory to employ a single long loop of tubing rather than the multiple tubes.

During the course of actual respiration flow passes alternately in each direction through the pneumotachograph 11 and likewise flows through the chambers 55, 57 and the tubes 61 alternately back and forth at a fraction of the rate through the pneumotachograph 11. By proper selection of the size of the tubes 61 and the chambers 55, 57 together with the assistance of the baffles 59 to retard mixing in the chambers, the chamber 55 will always contain a sample which is an average of the gas which is passed from left to right through the pneumotachograph 11. The chamber 57 will always contain a sample which is an average of the gas which is passed from right to left through the pneumotachograph 11.

By means of taps 63 and 65 the gases in the chambers 55 and 57 may be sampled and their composition determined. The composition of the gas in the chambers 55 and 57 is an average of the expiration and inspiration gases and sampling can therefore be done at a relatively slow rate, the gas composition not changing rapidly over several breaths.

It should be recognized that the resistance of the pneumotachograph 11 is constant over a large range of flow and may be designated $R_1$. The resistance of the tubes 61 is also constant over a wide range since their small internal diameter causes a laminar flow. This resistance may be designated $R_2$. The number, size and length of the tubes 61 are chosen such that $R_2$ is much greater than $R_1$ and it has been found convenient to make $R_2$ fifty to one hundred times greater than $R_1$. Flow through the pneumotachograph 11 and tubes 61 are inversely proportional to their respective resistances. Thus, if $R_2$ is one hundred times greater than $R_1$, the flow through the pneumotachograph 11 will be exactly 100 times the flow through the loop 61 and the total flow will be 1.01 times the flow through the pneumotachograph or one hundred and one times the flow through the tubes 61.

With the above factors known for any specific embodiment of the invention, it can be seen that calculation of oxygen uptake is an easy matter. The total flow of gases can be calculated by known means from the reading of the differential pressure gauge 39. The quantitative composition of both expired and inspired gases can be determined by connecting the taps 63 and 65 to a gas analyzer (as shown with respect to another embodiment in FIG. 2) and multiplying the readings thereof by a multiplier based upon the relative resistance of the pneumotachograph 11 and tubes 61.

The actual sizes, volumes and so forth of the chambers 55 and 57 and tubes loop 61 may vary considerably with the expected respiratory rate and volume. As an example, it may be assumed that a particular patient expires about one liter per breath. If the resistance of the tubes 61 is one hundred times the resistance of the pneumotachograph 11, about 10 ml. will flow through the tubes 61 during each expiration. If the tubes 61 have a total volume of about 50 ml. it will be seen that the expired gases will move through the tubes 61 only about one-fifth of their length before expiration is complete and the direction of flow reverses due to inspiration. Thus, gases from the chambers 55 and 57 never intermix.

The exact shape of the chambers or the configuration of the tubes 61, or even of the pneumotachograph are not important to the invention. In fact the resistance of the tubes 61 can be supplied by other means, including a pneumotachograph like element of very high resistance such as set forth in FIG. 2.

Figure 2:
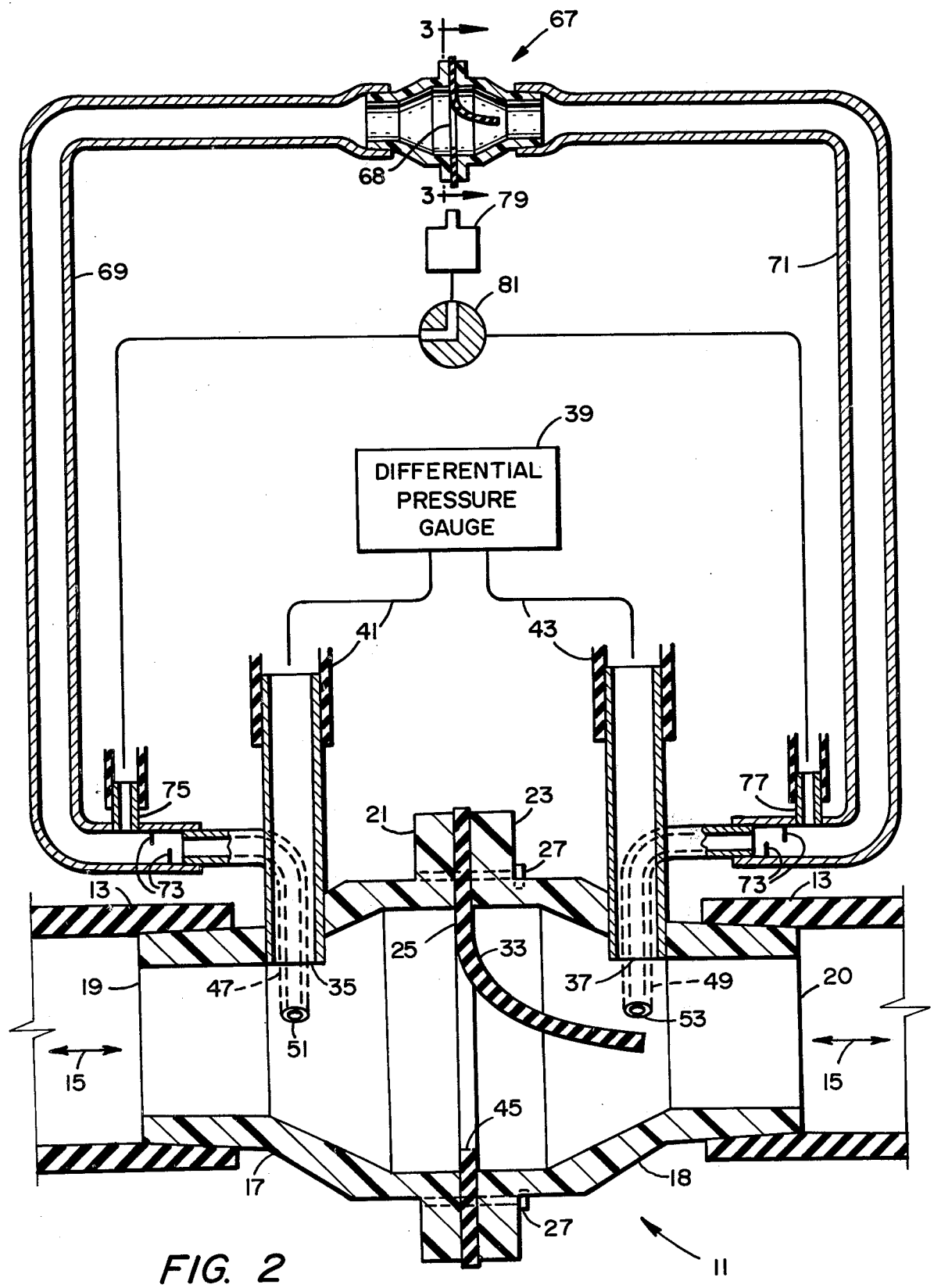
FIG. 2 is a schematic diagram of another apparatus for measuring oxygen uptake and respiratory quotient in accordance with the invention but wherein the high resistance path is provided by the use of an additional pneumotachograph.

In the embodiment shown in FIG. 2 elements identical to those of the embodiment shown in FIG. 1 are identified with like reference numerals and are not further described.

In the embodiment of FIG. 2 the high resistance can be provided by an element 67, similar to a pneumotachograph but without lines to a pressure gauge since flow rate therethrough need not be measured. The resistance element includes an orifice membrane 68 shown more clearly in FIG. 3 and more fully described in said U.S. Pat. No. 4,083,245. The resistance element 67 is connected to the tubes 47,49 through relatively elongated chambers 69 and 71 each of which carries baffles 73. The baffles 73 serve the same purpose as the baffles 59 in the embodiment shown in FIG. 1 and the resistance element 67 serves the same purpose as the tubes 61. The size of the resistance element 67 is considerably smaller than that of the pneumotachograph 11 whereby its resistance is considerably greater than that of the larger unit. Again, the path from the opening 51 through the chamber 69, resistance element 67 and chamber 71 to the opening 53 has sufficient volume and includes sufficient baffles 73 that they are never completely flushed during a single breath. A slug of gas moves back and forth through the pneumotachograph 67 with boundary interfaces somewhere within the chambers 69 and 71 but essentially never mixing in any large way with the gases in those chambers.

To actually calculate the oxygen uptake samples are taken from the chambers 69 and 71 through the taps 75 and 77, respectively, leading to a gas analyzer 79 through a valve 81. It need only be necessary to assure that the volumes drawn for sampling are sufficiently small that there is no appreciable effect on the concentration of the gases in the chambers 69 and 71.

The apparatus of the invention replaces the Douglas Bags and spirometers of early methods and can be made very small and portable. Even so the device of the invention gives valid samples for measurements which are very reliable and do not require the use of rapid gas analyzers. The invention provides a method for making measurements which greatly reduces the bulk of the bags or tubing required and the gas analyzers need have a response time of only about 15 or 20 seconds. Moreover, the devices are simpler, lighter and less susceptible to difficulty from saliva contamination and leaks than are the devices of the prior art.

What is claimed is:

1. Apparatus for use in a system for measuring oxygen uptake and the like comprising first conduit means for conducting flow of respiration gases to and from a patient, said first conduit means including first flow resistance means, second conduit means having one end thereof in communication with said first conduit means on one side of said first flow resistance means and the other end thereof in communication with said first conduit means on the other side of said first flow resistance means, said second conduit means including second flow resistance means, the volume of said second conduit means being substantially greater than the volume of gases conducted therethrough by a single breath of the patient whereby flushing of the second conduit means is precluded, and sampling means coupled adjacent the ends of said second conduit means for analyzing the gases therein.

2. Apparatus as defined in claim 1 wherein said second flow resistance means affords substantially greater resistance to the flow of gases than said first flow resistance means.

3. Apparatus as defined in claim 1 wherein said first flow resistance means comprises the flow resistance of a pneumotachograph.

4. Apparatus as defined in claim 1 wherein said second flow resistance means comprises an elongated tube.

5. Apparatus as defined in claim 1 wherein said second flow resistance means comprises a series of elongated tubes arranged in parallel.

6. Apparatus as defined in claim 1 wherein said second flow resistance means comprises a housing having inlet and outlet ports and an orifice membrane disposed across the interior of said housing between said inlet and outlet ports, said orifice membrane being formed of an elastic material, said orifice membrane defining an orifice, a flap disposed within and substantially coextensive with said orifice and having one edge thereof integral with said membrane to thereby form a hinged connection between said flap and said membrane, said flap including sides which converge to form the narrowest portion of the flap at that portion thereof most remote from the hinged connection to the orifice membrane, said hinged connection being narrower than the widest portion of said flap.

7. Apparatus as defined in claim 1 wherein said first and second flow resistance means each provide a constant resistance to the flow of respiration gases over a wide range of flow velocity.

8. Apparatus as defined in claim 1 wherein said second flow resistance means affords resistance to the flow of gases fifty times greater than does said first flow resistance means.

9. Apparatus as defined in claim 1 wherein said second flow resistance means affords resistance to the flow of gases one hundred times greater than does said first flow resistance means.

10. Apparatus as defined in claim 1 wherein said second conduit means comprises a first chamber at one end thereof and a second chamber at the other end thereof, said second flow resistance means being disposed in communication between said chambers, said sampling means being coupled to said chambers.

11. Apparatus as defined in claim 10 together with baffle means disposed within said first and second chambers.

* * * * *